(12) United States Patent
Dumont et al.

(10) Patent No.: US 9,724,006 B2
(45) Date of Patent: Aug. 8, 2017

(54) SYSTEMS AND METHODS FOR THE ADAPTIVE DIAGNOSIS OF HEART FAILURE

(71) Applicant: SORIN CRM SAS, Clamart (FR)

(72) Inventors: Jérôme Dumont, Chatillon (FR); Oliver Baumann, Southampton (GB)

(73) Assignee: SORIN CRM SAS, Clamart (FR)

( * ) Notice: Subject to any disclaimer, the term of this patent is extended or adjusted under 35 U.S.C. 154(b) by 567 days.

(21) Appl. No.: 14/191,093

(22) Filed: Feb. 26, 2014

(65) Prior Publication Data

US 2014/0243690 A1    Aug. 28, 2014

(30) Foreign Application Priority Data

Feb. 26, 2013    (FR) ...................... 13 51664

(51) Int. Cl.
| | |
|---|---|
| A61B 5/02 | (2006.01) |
| A61B 5/04 | (2006.01) |
| A61N 1/39 | (2006.01) |
| A61N 1/37 | (2006.01) |
| G06F 19/00 | (2011.01) |
| A61B 5/0205 | (2006.01) |
| A61B 5/00 | (2006.01) |

(52) U.S. Cl.
CPC ........ *A61B 5/04012* (2013.01); *A61B 5/0205* (2013.01); *A61B 5/7275* (2013.01); *A61N 1/37* (2013.01); *A61N 1/3925* (2013.01); *G06F 19/345* (2013.01)

(58) Field of Classification Search
CPC .......... A61N 1/3925; A61N 1/37; A61B 5/04; A61B 5/00; A61B 5/0205; A61B 5/7275; A61B 5/04012; A61B 5/7264; G06F 19/345; G06F 19/3431
See application file for complete search history.

(56) References Cited

U.S. PATENT DOCUMENTS

| | | | | |
|---|---|---|---|---|
| 5,005,143 | A | * | 4/1991 | Altschuler ............ G06F 19/345 702/181 |
| 6,269,353 | B1 | * | 7/2001 | Sethi ........................ G06N 3/02 706/20 |
| 2002/0029002 | A1 | | 3/2002 | Bardy |

(Continued)

FOREIGN PATENT DOCUMENTS

EP    1 867 360 A2    12/2007

OTHER PUBLICATIONS

Preliminary Search Report for French Patent Application No. 1351664, dated Sep. 4, 2013, 2 pages.

*Primary Examiner* — Navin Natnithithadha
*Assistant Examiner* — Eric Messersmith
(74) *Attorney, Agent, or Firm* — Foley & Lardner LLP

(57) ABSTRACT

A cardiac implant includes a classifier configured analyze the data for comparison to thresholds prioritized according to a Boolean decision tree. The implant can generate an indicator of alert status (i.e., alert or no alert). A supervisory device operated, for example, by a doctor can associate each indicator a marker (AE/no AE) indicating the presence or absence of an observed adverse event. In the presence of a false positive, a command for update of the thresholds of the decision tree is transmitted to the implant. A database of reference patients can be used to recreate or further update the decision tree to avoid the occurrence of false negatives.

22 Claims, 3 Drawing Sheets

(56) References Cited

U.S. PATENT DOCUMENTS

| | | | |
|---|---|---|---|
| 2003/0055461 A1 | 3/2003 | Girouard et al. | |
| 2004/0193036 A1* | 9/2004 | Zhou | G06F 19/345 600/407 |
| 2005/0216067 A1 | 9/2005 | Min et al. | |
| 2006/0010090 A1 | 1/2006 | Brockway et al. | |
| 2006/0184496 A1 | 8/2006 | Wang et al. | |
| 2007/0260285 A1* | 11/2007 | Libbus | A61N 1/36114 607/9 |
| 2012/0157856 A1 | 6/2012 | An et al. | |
| 2013/0116578 A1* | 5/2013 | An | A61B 5/0205 600/484 |
| 2015/0363709 A1* | 12/2015 | Kamei | G06N 99/005 706/12 |

* cited by examiner

SYSTEMS AND METHODS FOR THE ADAPTIVE DIAGNOSIS OF HEART FAILURE

CROSS-REFERENCE TO RELATED APPLICATION

This application claims the benefit of and priority to French Patent Application No. 1351664, filed Feb. 26, 2013, which is incorporated herein by reference in its entirety.

BACKGROUND

The disclosure relates to "active medical devices" as may be defined by Directive 93/42/EC of 14 Jun. 1993 the Council of the European Communities. This disclosure particularly relates to implantable pacing, resynchronization and/or defibrillation systems and methods for use in the diagnosis and treatment of cardiac arrhythmias.

The disclosure may relate to active devices which may be implanted or devices that conduct analytic processing for purely or primarily diagnostic purposes—e.g. external systems for home monitoring of patients (clinical evaluation, home monitoring or remote monitoring). Such devices may, for example, form a wireless connection to an interrogation device disposed near the wearer of the device. The wireless connection may be activated at regular intervals, e.g. daily, to download and transmit the data collected by this device to a remote site station for analysis. This disclosure can also relate to the diagnosis of early cardiac decompensation events (events hereinafter referred to as "Adverse Events" or AE) using computerized methods for analysis of signals collected by the device.

The early detection of cardiac decompensation is a complex issue, reflected in a patient by multiple physiological parameters that may be evaluated and analyzed to optionally issue an alert. Some physiological parameters and symptoms associated with such cardiac decompensation may include:

The presence of fluid in the lungs, which may produce a decrease in respiratory amplitude and in the transthoracic impedance;

An acceleration of the respiration rate, in particular earlier during effort;

Weight gain and fatigue felt by the patient, leading the patient to exercise less, or to less intensely exercise, with a lower maximum heart rate;

A decrease in ejection fraction;

A decrease in the heart rate variability;

Changes in various morphological parameters of endocardial electrogram signals (EGM) and/or of endocardial acceleration signals (EA); and The presence of episodes of atrial fibrillation (AF), especially conducted AF, which is also an important potential source of cardiac decompensation.

It can be seen that one can thus evaluate a large amount of data related to the clinical condition of the patient. This data can be derived from the electrical activity of the myocardium, can include EGM signals collected by implantable electrodes, can include EA or cardiac bioimpedance signals, or can include signals reflecting changes in various parameters such as heart rate, ventilation amplitude and frequency, activity, etc. obtained from measurements by activity sensors (accelerometer G sensor) and/or physiological sensors (minute ventilation MV sensor). The history for this data can be determined, for example, daily. However, taken separately, analysis of daily indicators does not necessarily give good results.

Some combinations of these indicators can provide better analytical results. Numerous indexes can be developed for this purpose. EP 1867360 A2 (assigned to Sorin CRM S.A.S, previously known as ELA Medical) teaches crossing information from MV and G sensors with an endocardial acceleration or a cardiac bioimpedance signal. An algorithm creates a risk index of cardiac decompensation. The system generates a preventive warning composite indicator, relative to different levels, depending on the indexes produced by the algorithms.

The cardiac decompensation prevention algorithms used so far, however, can generate a relatively high number of false alarms. These are usually false positives, which are irrelevant to the doctor but may unnecessarily worry the patient. However, the consequences of repeated false alarms can be important when the device not only delivers an alert (diagnostic function), but also changes its operation to suit the supposed improvement or worsening of the patient's condition, e.g. by reprogramming some of the functions of the device or by automatic modification of triggering thresholds.

Settings of the different criteria for triggering the alert is usually adjusted by varying parameters (thresholds), incremental parameters (minimum or maximum percentage increase), or meta-rules used to analyze the evolution of the indexes and their combination over several days.

U.S. 2006/0010090 A1 describes an expert system comprising a plurality of thresholds corresponding to the various information collected by an implantable device. A practitioner can modify these thresholds, e.g., using information provided by the expert system to describe the history of the patient. It is thus possible to increase the selectivity of the system and avoid triggering an untimely alarm. This proposal however, does not take into consideration that the sensitivity and specificity (that is to say, the selectivity of the analysis) are generally regarded as two antagonist notions. In other words, with many known algorithms increased sensitivity is usually accompanied by a lower specificity—with correspondingly an increased risk of false alarms ("false positives"). Conversely, if the warning criteria are more stringent, cases of false positives are reduced, but with the risk of not triggering an alert in critical cases ("false negatives"), a situation that should be avoided as much as possible.

The object of the invention is to provide improved systems and methods for adapting an algorithm that prevents cardiac decompensation.

SUMMARY

Systems and methods of the present disclosure advantageously utilize an evolutionary evaluation for a given patient, according to the false alarms and/or missed alerts previously encountered in this patient, so as to no longer reproduce them. More specifically, and as is described in more detail below, the invention discloses a technique for such an adaptive algorithm that takes into account both:

False positives (the most common errors), by directly updating the device after these false positives were identified as such by a doctor, this update being made by an adjustment of parameters used by the algorithm; and False negatives (less frequent but very problematic errors), by a more profound adaptation of the algorithm, from a panel of control patients whose profile is stored in a database, and have been identified as having similar behaviors to the current patients.

U.S. 2005/0216067 A1 (Pacesetter, Inc.) describes some algorithms that implement linear combinations of various parameters. U.S. 2003/0055461 A1 (CPI) also describes one possible algorithm for calculating at least some of the weighting factors for a linear model.

Linear algorithms, however, can be sub-optimal when the purpose is to assess the risk of occurrence of cardiac decompensation. Put one way, linear algorithms are sub-optimal when the system they are used to describe is not linear. For example, the presence of episodes of atrial fibrillation (AF) is an important indicator, which should be accorded a high weighting when the daily duration of these episodes is important. On the other hand, the absence of AF does not mean that the risk of decompensation is low.

To overcome these limitations, the invention proposes to implement a non-linear method (unlike those described in the abovementioned documents), based on a decision tree. The method includes maintaining prioritized thresholds. The method can include a succession of tests corresponding to comparisons of different parameters in relation to thresholds. The succession of tests can be combined by a series of logical ANDs, the result of which is a binary result of the type "warning/no warning." This nonlinear method based on a decision tree can have the following dual advantages, among others: (1) better early detection of risks of cardiac decompensation relative to linear algorithms because the method better addresses the various cases of decompensation that have been clinically observed, and (2) is adjusted over time, as it starts from a generic algorithm which is then refined over time as a function of specific data observed for the concerned patient.

More specifically, the invention discloses a system including:
a) an active medical device such as a pacemaker, a resynchronizer, a defibrillator and/or an apparatus for diagnostic purposes, including:
  sensors (100-106) for acquiring, processing and storing data of a clinical status of a current patient wearing the medical device, these data being multimodal data related to heart activity and evaluated at successive predetermined time intervals;
  a microprocessor having a classifier (108) adapted to analyze said data to compare the data to a set of thresholds and in response to generate an indicator (112) of alert or no alert;
  memory for storing the successive indicators generated by the classifier means; and
  on the microprocessor, a module (114) for updating said thresholds in response to reception of an external command (e.g., via a communications interface),
b) a communication device external to the active medical device, including:
  communication electronics adapted to transmit to said external medical device command for said updating of the thresholds, and
c) a data system (e.g., an external data system at a research facility), including:
  a memory storing a database (302) of reference patients, storing for each reference patient a set of said clinical status data with associated markers indicating the presence or absence of an adverse event; and
  an interface (e.g., a communications interface, a user input interface, etc.) for inputting a set of clinical status data of the current patient (300), with associated markers indicating the presence or absence of an adverse event.

The thresholds may be successively prioritized thresholds according to a Boolean decision tree configuration (110);
  The communication device can include a supervision module (200) configured to, for each of the indicators generated by the classifier:
  i) input a marker (AE/no AE) indicating the presence or absence of a deleterious event observed during the time interval corresponding to the respective flag,
  ii) input a notation (true/false positive/negative rating) indicating (according to the corresponding value of the marker) if the alert or absence of alert of the indicator represents: a true positive, a true negative, a false positive or a false negative, and
  iii) associate with each indicator the marker and its corresponding notation.

The communication device can further be configured to, for the correction of a false positive, transmit to the classifiers of the medical device a command for shifting the threshold values that triggered the alert.

The external data system may include, for the correction of false negatives:
  a selection module (304) for extracting from the database a reduced group of significant reference patients (306). The selection may occur by comparing the clinical status data of the current patient with the clinical status data of a larger set of reference patients. The comparisons may be performed separately for the data for which the associated marker indicates the presence of an adverse event and those for which the associated marker indicates the absence of an adverse event;
  a decision creation tree module (308) configured to define said successive thresholds of the decision tree and to prioritize these thresholds according to, for example, a Boolean configuration; and
  communications electronics to transmit to the classifier of the medical device the decision tree thus created.

The clinical status data may include data assessed on a predetermined time interval from variables among, e.g.: an average of the resting heart rate and exercise heart rate; an average of the maximum heart rate reached during each exercise; an average respiratory rate at rest and at exercise; an average maximum respiratory rate reached during each exercise; a time spent in atrial fibrillation; a ventilatory amplitude during exercise and at rest; an amount of exercise measured by an accelerometer; a heart rate variability; a variability of morphological parameters of endocardial electrogram signals; and/or a variability of morphological parameters of endocardial acceleration.

A cardiac implant collects multimodal clinical status data (100-106). Classifier means (108) analyze these data to compare them to thresholds prioritized according to a Boolean decision tree configuration (110), and generate an indicator (112) of alert or no alert. Supervision means (200) by a doctor allow associating to each indicator a marker (AE/no AE) indicating the presence or absence of an observed adverse event, and a notation (true/false positive/negative) indicating whether the alert or absence of alert of the indicator is a true positive, a true negative, a false positive or a false negative. In the presence of a false positive rating, a command for update (114) of the thresholds of the decision tree is transmitted to the implant. A database of reference patients (302) is also used to re-create (304-308) the decision tree to avoid the occurrence of false negatives.

DETAILED DESCRIPTION

Embodiments of the invention may be implemented using microcontrollers or digital signal processors. For the sake of clarity, the various processing applied will be broken down and diagrammed by a number of different functional blocks in the form of interconnected circuits or modules (e.g., computer code modules executable and stored in non-transient computer-readable media), however this representation is only illustrative.

With regard to the medical device used in connection with this technique, the invention can be implemented with appropriate programming of the control software of a cardiac implant of a known type, for example a cardiac pacemaker, resynchronizer and/or defibrillator, comprising means for acquiring a signal provided by endocardial leads and/or one or more implanted sensors. The invention can particularly be applied to implantable devices such as those of the Reply and Paradym families produced and marketed by Sorin CRM, Clamart, France.

These devices include a programmable microprocessor including circuitry to receive, form and process electrical signals collected by implantable electrodes, and to deliver stimulation pulses to these electrodes. It is possible to transmit by telemetry software that will be stored in memory and executed to implement the functions of the invention that will be described below.

Although we speak later of "implant," the invention is not limited to this type of device and can be implemented with external devices, for example devices for substantially diagnostic purposes collecting and storing various information to be analyzed to assess the clinical status of a patient.

As indicated in the introduction, the object of the invention is to implement an analysis technique of data related to the clinical status of a patient wearing a medical device, usually an implantable device, allowing the delivery (or not) of a preventive cardiac decompensation alert.

Decision Tree

Specifically, the technique of the invention is based on a non-linear type analysis of these clinical status data, specifically a data analysis by comparison to a set of hierarchical successive thresholds according to a Boolean decision tree configuration, leading to the result consisting of the issuance of a binary indicator "alert/no alert."

Figure 1:
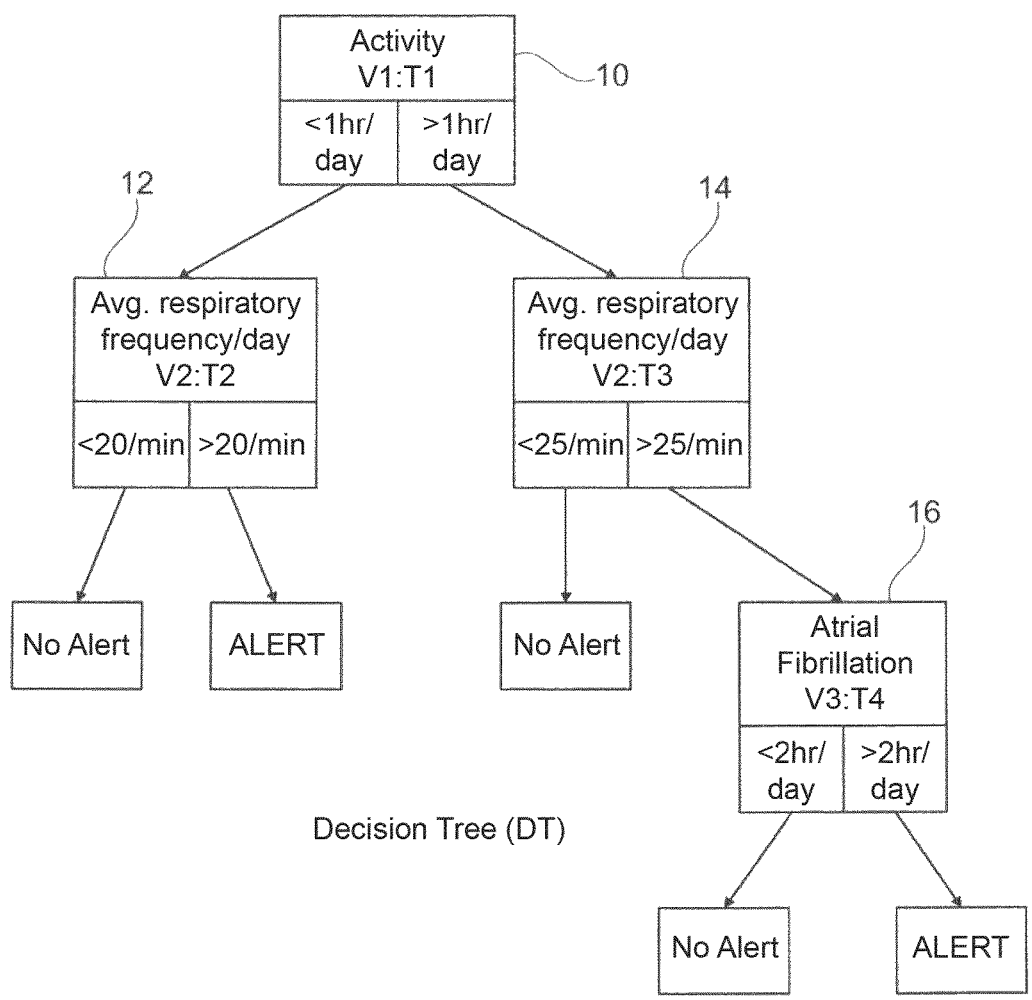
FIG. 1 is an example of a decision tree created according to the described systems and methods. The decision tree is configured to analyze various data of the patient's clinical status for generating in response a warning indicator or a no warning indicator.

FIG. 1 illustrates an example of such a decision tree (DT, Decision Tree), which shows the method to prioritize the comparisons to the different thresholds, each comparison binary determining the crossing or not of the considered threshold and, depending on the result, leading to a conditional branch to other comparisons to other thresholds, and so on until the production in response of the warning final indicator or of the no warning final indicator.

In the simplified example shown, the first data tested (block 10) is the level of daily activity V1, which is compared to a first threshold T1. In the illustrated example, the threshold T1 is set at less than or greater than 1 hour of activity per day. For V1 activity below this threshold T1, the following test (block 12) will focus on the daily average respiratory rate V2, tested against a threshold T2. In the illustrated example, the threshold T2 is less than or greater than 20 breaths per minute. If this threshold is not crossed, the algorithm produces an indicator "no warning," but if the threshold is exceeded the indicator will be "warning" (that is to say, an early warning of cardiac decompensation, indicating the presence—according to the algorithm—of a risk of short-term occurrence of an episode of cardiac decompensation).

In the case of activity V1 exceeding threshold T1, the respiration rate V2 is compared (at block 14) to a threshold T3, which is different from the previous threshold T2. This threshold is, for example, 25 breaths per minute. If it is not crossed, the indicator produced is "no warning." Otherwise, a further test is made (block 16) on a third data V3, namely the average daily duration spent in atrial fibrillation, which is compared to a threshold T4. If this threshold is not crossed, the indicator will be "no warning", otherwise a "warning" indicator will be produced.

Such a decision tree can be formalized by a Boolean relation which, in the example described above, is:

Alert=(V1<T1 & V2>T2)+(V1>T1 & V2>T3 & V3>T4)

Such a decision tree may be extended to the analysis of a large number of clinical data of the patient status. Such data may be related to the cardiac and hemodynamic activity of the patient and evaluated on successive intervals of predetermined time, e.g. daily.

An algorithm such as the one described above with respect to the classifier can produce a "warning" or "no warning" indicator from the clinical status data automatically analyzed, but this indicator does not necessarily reflect the physiological and clinical reality (e.g., the presence or absence of a true deleterious event (AE, Adverse Event), confirmed from the clinical point of view).

As applicable, for each alert indication or absence of alert generated by the decision tree, one can find the presence of a true/false positive/negative, with four possibilities summarized in the following Table 1:

|  | Alert | No alert |
| --- | --- | --- |
| AE | True positive | false negative |
| No AE | false positive | true negative |

Systems and methods described herein can use this determination, which may be input by a physician after manual inspection of the alerts relative to the actual data, to dynamically adapt the different thresholds of such a decision tree. These adaptations may be based on proven false positives, in order to improve the selectivity of the algorithm over these successive adaptations. Systems and methods described herein can also construct or reconstruct the decision tree. Such reconstruction may be conducted, for example, in the presence of proven false negative. The construction or reconstruction may create the sequence of the branches of the tree, as may be represented by or described by a Boolean equation, and the construction or reconstruction may also set or adjust the level of the different thresholds.

Figure 2:
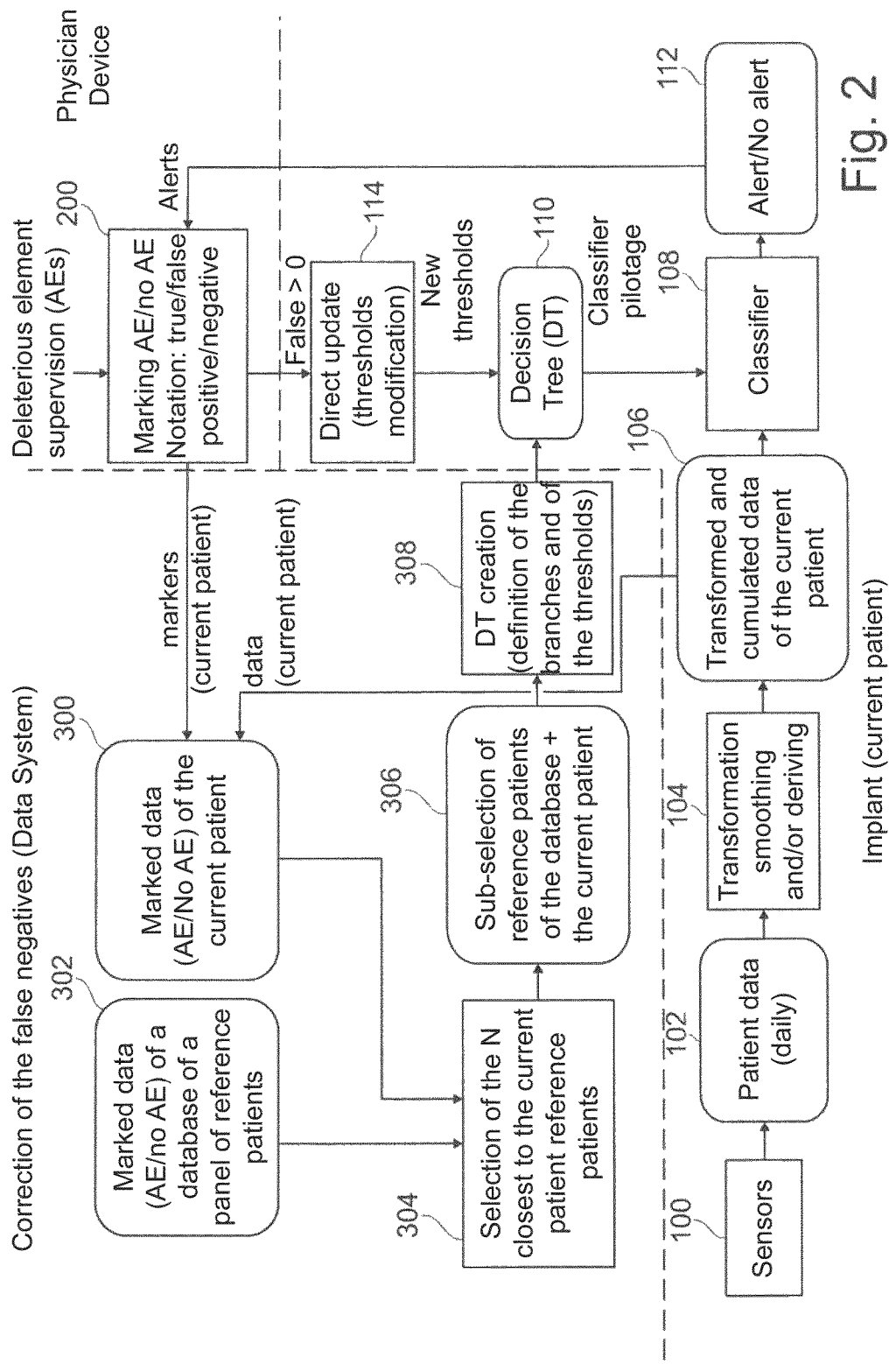
FIG. 2 is a schematic diagram of a system configured to operate according to the methods described herein.

FIG. 2 is a block diagram of a system and method according to an embodiment of the invention. FIG. 2 particularly illustrates a system and method that can adapt the decision tree (configuration of the branches and thresholds) to reduce false positives and false negatives, and thus improve the performance of the algorithm for early warning of cardiac decompensation. FIG. 2 illustrates the following components as a part of the system: (a) The device carried by the current patient (e.g., an implanted active medical device) that can continuously collect and process the different clinical condition data: blocks 100-114; (b) a supervision module utilized by a physician: block 200; (c) a separate system for correcting false negatives implementing a database and a learning engine: blocks 300-308.

Operations Performed Within the Implant

The implant collects data from a patient using sensors (block 100). The sensors may provide, for example, data regarding electrical activity of the myocardium, including intracardiac electrogram (EGM) signals. The sensors may also or alternatively provide, for example, hemodynamic activity signals, such as endocardial acceleration signal (EA) or cardiac bioimpedance signal. The sensors may also or alternatively provide, for example, signals reflecting variations of various parameters (heart rate, ventilation amplitude and frequency, activity, etc.) during an alternation of stages of stress and recovery stages, determined by the physical sensor (accelerometer G) or physiological sensor (minute ventilation MV) giving an indication of this level of activity. Other signals may be provided from sensors such as pressure sensors, oxygen saturation in the blood sensors, etc., depending on the patient's hemodynamic status.

Sensor data may be collected on a predetermined time interval, e.g. daily, and processed (block 102) to produce clinical status data such as, for example:

Average of the heart rate at rest and during exercise;
Average maximum heart rate reached during each exercise;
Average respiratory rate at rest and during exercise;
Average maximum respiratory rate reached during each exercise;
Time spent in atrial fibrillation;
Ventilation amplitude during exercise and at rest;
Amount of exercise as measured by an accelerometer;
Heart rate variability;
Variability of morphological parameters of the EGM signals, and/or
Variability of morphological parameters of the EA signals.

Such data may be processed (block 104), for example, by de-noising or conducting temporal smoothing on windows of variable size. Other processing may include determining a sensor's temporal variation, for example, by calculating slopes, by linear regression, or by comparing a short-term average (7 days) to a long-term average (30 days). The same variable may be separately, firstly, smoothed and, secondly, derived, resulting in two different transformed data from the same variable but represented in two different methods.

Thus, for a given patient (hereafter "current patient"), a database is formed (block 106) of temporal series of variously transformed (or raw) clinical state data (obtained from the processing by the block 104).

This data is then analyzed by a classifier 108 operating under the control of a decision tree 110 as that described above in example with FIG. 1. This classifier uses the decision tree 110 recorded in the implant to distribute the latest data processed in the "alert" or "no alert" classes (block 112).

The successive alerts (or "no alert" signals) and the matching temporal data may be transmitted at regular intervals (e.g., every day). Such signals and matching data may be subsequently analyzed (block 200) by a doctor who oversees the patient. In other words, daily data history and the classifier's output that is stored in the implant may be transmitted to a physician's system in order to detect the presence or absence of deleterious events AE.

The purpose at this stage is to make a supervised classification. In other words, the physician can conduct a classification to confirm or deny the classification conducted by the implanted device. The actual occurrence of AE is known and documented by the physician. Following this step, the system knows where the actual AE are in the temporal series produced and stored by the implant (block 106). When an AE is proved by the doctor, the latter examines whether a corresponding alert was generated or not by the classifier 108 and assigns a "true positive" rating if the implant has actually produced an alert, and a "false negative" otherwise. He also examines the series of alerts that have been produced by the classifier: if indeed the period showed a higher risk of cardiac decompensation for the patient (proven or imminent AE), then the doctor indicates a "true positive" rating, in otherwise, a "false positive" rating. Each proved AE and each alert generated and saved by the implant is thus associated with a true/false positive/negative rating in a memory device (e.g., according to Table 1 above).

Update of the Decision Tree Thresholds

In the case of a false positive identified by the analysis performed by the doctor, the physician device may directly perform an update of the decision tree in the implanted device by modifying the thresholds of the decision tree (block 114). The adjustments can be estimated to avoid the subsequent production of false positives of the same type. The updated thresholds may be the thresholds that triggered an alert, which may be automatically modified (block 114) by the direct updating algorithm.

Figure 3A:
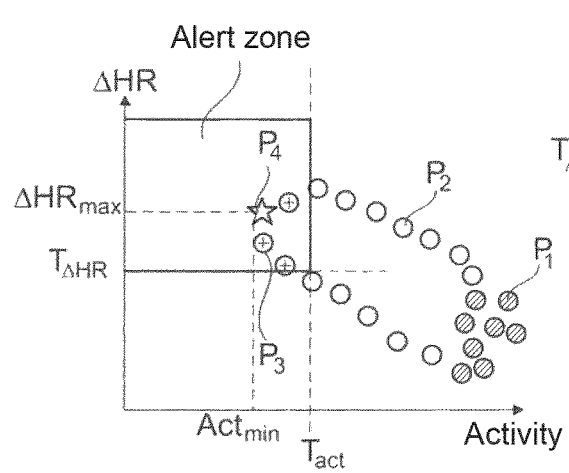
FIGS. 3a and 3b illustrate the technique of direct update by changing the thresholds of the decision tree to increase the specificity of the alert.
Figure 3B:
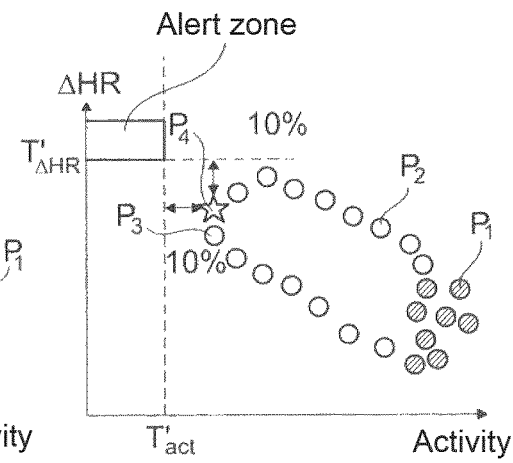

An example of providing an update of thresholds is illustrated in FIGS. 3a and 3b. These Figures illustrate a representation of two different pieces of data, namely the daily time spent in activity ("Activity") and the heart rate variability ("HR").

In the case of FIG. 3a, which corresponds to the situation that triggered a false alert (false positive), the daily data is represented by a cloud of points. The hatched points $P_1$ correspond to an initial condition of the patient with high activity and low variability, reflecting good clinical condition. Then (as illustrated by not hatched points $P_2$), the activity decreases and the variability of heart rate increases. The points enter the alert zone (defined by the thresholds $T_{act}$ and $T_{\Delta HR}$): points $P_3$ marked with a "+" and point $P_4$ are the the farthest from the current thresholds $T_{act}$ and $T_{\Delta HR}$ (point of coordinates $\Delta HR_{max}$, $Act_{min}$). The research of point $P_4$ may be carried out in particular by normalizing the data, then by calculation of the Euclidean distance (e.g., from the thresholds).

If the doctor has determined that the alerts occurring at points $P_3$ and $P_4$ is a false alert (false positive), then in response to this determination, the thresholds $T_{act}$ and $T_{\Delta HR}$ are modified, e.g. offset so as to leave a 10% margin relative to the point $P_4$. The new thresholds thus become, as shown in FIG. 3b: for the activity: $T'_{act}$=90% of $Act_{min}$ and for $\Delta HR$: $T'_{\Delta HR}$=110% $\Delta HR_{max}$. The alert zone is then redefined at a sufficient distance from the point $P_4$, such alert zone estimated to not produce false positives later.

This type of correction by shift of the thresholds may not be applicable in case of false negative, because the algorithm cannot know the terms of the Boolean equation for the decision tree that should have triggered the alert. It is also not desirable to globally change all thresholds. In this case, it may be preferable to re-create a decision tree.

Creation/Re-Creation of the Decision Tree

This re-creation of the decision tree may be performed offline by a data processing system (e.g., at a clinic using a clinic computing system, at an offsite location using a server computer). The process is shown to include comparing (block 300) the marked (AE/no AE) and doctor scored (true/false positive/negative) current patient data, to a labeled data base (AE/no AE) for a significant range of reference patients. In an exemplary embodiment, the reference patients' data was previously recorded and analyzed. Such data may include known dates of cardiac decompensation, helping to mark (AE/no AE) and judge this reference clinical status data.

The collective data (of the current patient and of the panel of reference patients) are applied to a selection module (block 304) of the N reference patients the closest to the current patient. In other words, the system conducts a selection of patients having, relative to the current patient: i) profiles of similar base clinical status data, and/or ii) a comparable behavior as it relates to the occurrence of an AE. The selection of these N reference patients may be made, for example by analyzing a metric (e.g., of the Bregman distance type). This selection may be made separately for periods with AE and for periods without AE.

Figure 4:
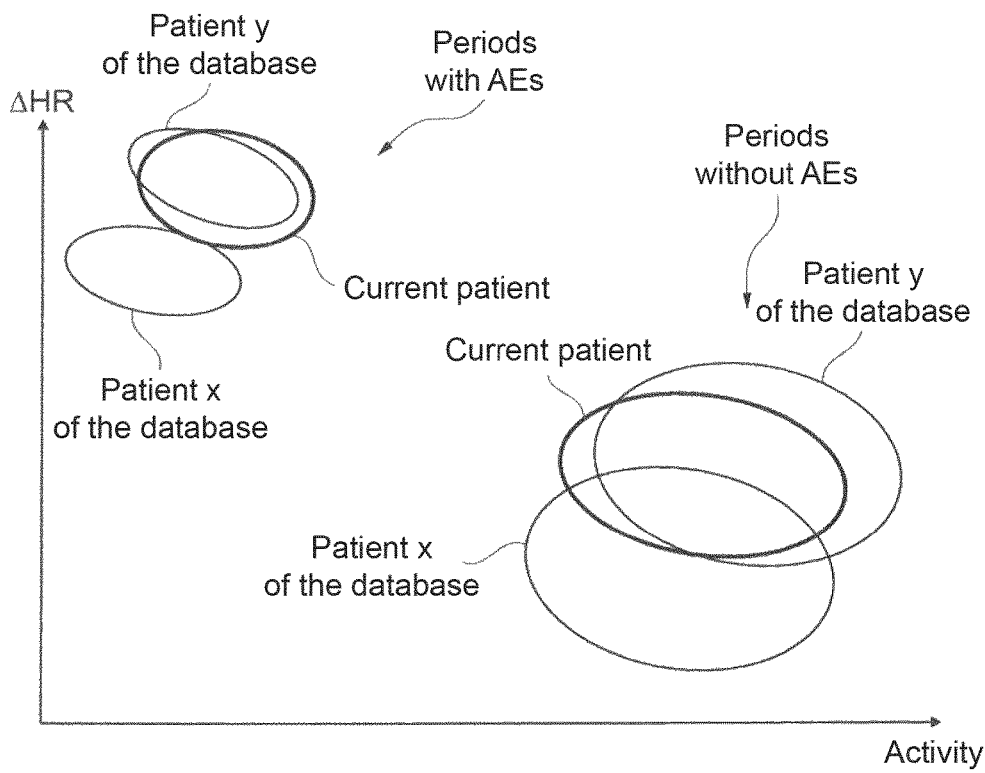
FIG. 4 shows a method for selecting a panel of reference patients who are the closest to the current patient. The method may include selecting separately for periods with adverse events and for those without deleterious events.

FIG. 4 illustrates such a selection example. The illustrated data includes a representation of daily time spent in activity ("Activity") and of the heart rate variability ("ΔHR"). For each reference patient of the database, a ranking position relative to the current patient may be assigned by an algorithm including the steps of:

Calculation of the distances between each AE of the current patient and each AE of the reference patients;
For each reference patient and for each AE of the current patient, selection of only the shortest distance;
Determination for each AE of the current patient of the ranking of the reference patients; and
Assessment of the average rank between the current patient and the reference patients (mean of the ranks of each of the AE).

The reference patient selection may be based on the comparison of "AE" data and "no AE" data of the current patient, represented by a multivariate Gaussian, with the data of the reference patients. Bregman distance may be used as distance between the distributions, which may facilitate taking into account the covariances in addition to the averages.

The patients are then sorted according to the inverse of their distance from the current patient, separately for the periods with AE and periods without AE. Specifically, the "AE" periods correspond, for example, to the data measured J days before the onset of the AE (e.g. J=10 days). The "no AE" data may be the data measured over periods of M months, e.g. M=2 month except during the month preceding an AE.

Depending on the number of periods with AE or without AE, several options may arise:

If several periods with AE or several periods without AE are found for a reference patient, it the closest period to the current patient will be taken into account;
In the case of several periods with AE in the current patient, the average of the ranks of the different AE will be performed, but the last reference period will always be taken into account.

Once a rank has been assigned to each reference patient, for the periods with/without AE, the "period with AE" and "period without AE" ranks are averaged. The reference patients may then be classified. A reduced number N may then be selected (block 306), e.g. N=15 to 20 reference patients, which will be considered to be the closest to the current patient.

The data corresponding to the patients thus selected will be used to create a decision tree (block 308). The creation of the decision tree is to identify i) the different branches of the tree (definition of the Boolean equation) and ii) the level of the different thresholds to which the respective clinical status data are compared.

The decision tree may automatically be created by a learning module of N inputs (the different possible clinical status data) and two outputs (the alert/no alert binary indicator). The process may include excluding some series of data when it is not certain that the observed data are related to the occurrence of an AE (e.g. in a relatively early period before the onset of the AE).

The decision tree can be created for example by applying a Breiman algorithm as described by: Breiman L, Friedman J H, Olshen R and Stone C, Classification and Regression Trees, Boca Raton, Fla. During learning, weights are assigned to true/false positives/negatives in order to establish a frequency of false alerts not to exceed, for example, no more than two false positives per year per patient.

The decision tree thus created can be downloaded by telemetry into the implant (decision tree 110). Such download may occur, for example, during an update of the software during a visit to the doctor. Its implementation may advantageously reduce or minimize false negatives as well as false positives.

The invention claimed is:

1. A system for the diagnosis of heart failure, comprising:
(a) a medical device, comprising:
sensors comprising circuity that acquires data of a clinical status of a current patient carrying the medical device;
a memory device;
a processing circuit configured to execute instructions stored on the memory device to:
compare the data to a decision tree having thresholds,
generate an alert status indication in response to the comparisons, and
store the alert status indication in the memory device; and
update said thresholds in response to an external command;
(b) a data system not permanently coupled to the medical device, wherein the data system is configured to:
receive, from the medical device, the data and the alert status indication;
compare the data with a pool of reference patient data by comparing the alert status indication and a scoring indication of the alert status indication to the pool of reference patient data, the scoring indication indicating whether the corresponding alert status indication is a true positive, a false positive, a true negative, or a false negative;
automatically select a set of reference patients from the pool of reference patient data based on reference patients closest to the data based on the comparison;
determine, based on the set of reference patients, updates to the decision tree, wherein the updates are at least one of adding a branch, removing a branch or modifying thresholds of the decision tree;
transmit the updates to the decision tree to the medical device.

2. The system of claim 1, wherein the decision tree is a binary tree comprising at least one parent node decision and two child node decisions, and wherein the thresholds are prioritized thresholds for the binary tree.

3. The system of claim 2, further comprising:
a physician system separate from the medical device and the data system, wherein the physician system comprises a microcontroller for associating physician feedback with alert status indications and the data associated with the alert status;
wherein the physician system is configured to transmit information of the physician feedback as the accuracy determinations used by the data system.

4. The system of claim 3, wherein the physician system is further configured to use the physician feedback to transmit the external command to the medical device for updating the thresholds.

5. The system of claim 4, wherein the physician system is configured to receive inputs comprising:
i) a marker indicating the presence or absence of a deleterious cardiac event observed during a time interval, and
ii) a notation indicating, according to the corresponding value of the marker, if the alert or absence of alert of the indicator represents: a true positive, a true negative, a false positive or a false negative.

6. The system of claim 5, wherein the physician system is configured to, in the presence of a false positive rating, transmit to the classifier of the medical device a command for shifting the threshold values that triggered the alert having the false positive rating.

7. The system of claim 6, wherein the data system is configured to determine updates to the decision tree that are estimated to correct for false negatives by evaluating the pool of automatically selected reference patient data.

8. The system of claim 7, wherein the data system compares between the current patient's data and the data of the reference patients, these comparisons being performed separately for the data indicating the presence of an adverse event and data for which the an absence of an adverse event is indicated.

9. The system of claim 8, wherein the data system further comprises a decision tree creation module configured to define successive thresholds of the decision tree and to prioritize the thresholds according to a Boolean configuration.

10. The system of claim 9, wherein the data system further comprises communications electronics configured to transmit the updates to the decision tree to the medical device.

11. The system of claim 10, wherein the collected data comprises multimodal data related to heart activity and is collected at successive predetermined time intervals.

12. The system of claim 11, wherein the collected data comprises at least two of:
average of the resting heart rate and exercise heart rate;
average of the maximum heart rate reached during each exercise;
average respiratory rate at rest and at exercise;
average maximum respiratory rate reached during each exercise;
time spent in atrial fibrillation;
ventilatory amplitude during exercise and at rest;
amount of exercise measured by an accelerometer;
heart rate variability;
variability of morphological parameters of endocardial electrogram signals; and
variability of morphological parameters of endocardial acceleration.

13. A cardiac system comprising:
a cardiac implant comprising:
a microcontroller comprising a classifier configured to compare sensor data to thresholds prioritized according to a Boolean decision tree; and
communications electronics controlled by the microcontroller to send an indication of
whether the Boolean decision tree logic resulted in an alert for each set of stored sensor data;
a remote device configured to:
receive the sensor data and the indication;
compare the sensor data with a pool of reference patient data, by comparing the indication and a scoring indication of the indication to a plurality of reference patient data items in the pool of reference patient data, the scoring indication indicating whether the corresponding indication is a true positive, a false positive, a true negative, or a false negative;
automatically select a set of reference patients from the pool of reference patient data based on reference patients closest to the data based on the comparison;
determine, based on the set of reference patients, updates to the Boolean decision tree; and
transmit the updates to the Boolean decision tree to the cardiac implant;
wherein the microcontroller is configured to update the Boolean decision tree including the definition of the branch decisions and the thresholds in response to the updates to the Boolean decision tree received from the remote device via the communications electronics.

14. A method for the diagnosis of heart failure, comprising:
acquiring data using a medical device;
with the medical device, using the acquired data to classify portions of the data as associated with alerts;
communicating the portions of the data and the alert classifications to a remote device;
at the remote device:
receiving accuracy determinations for alert classifications and data set associations indicating alert classifications received from the medical device;
comparing a scoring indication based on the accuracy determinations and the data set associations with a plurality of reference patient data items in a pool of reference patient data, the scoring indication indicating whether the corresponding data set associations is a true positive, a false positive, a true negative, or a false negative;
automatically selecting a set of reference patients from the pool of reference patient data based on reference patients closest to the data based on the comparison;
determining, based on the set of reference patients, updates to the decision tree, wherein the updates are at least one of adding a branch, removing a branch or modifying thresholds of the decision tree; and
providing the determined updates to the medical device.

15. The method of claim 14, further comprising:
the medical device transmitting the portions of the data and the alert classifications to a third device separate from the medical device and the remote device; and
the third device processing the data and the alert classifications to generate the accuracy determinations provided to the remote device.

16. The method of claim 15, further comprising:
the third device using a user input element and a display for presenting the data to a user and receiving feedback from a user regarding whether or not an adverse event has been properly associated with a portion of data.

17. The method of claim 16, further comprising:
assigning a true positive rating if the medical device accurately produced an alert for a portion of data.

18. The method of claim 17, further comprising:
assigning a false negative rating if the medical device did not accurately produce the alert when it should have for a portion of data.

19. The method of claim 18, further comprising:
the third device using a user input element and a display for presenting the data to a user and receiving feedback from the user regarding whether or not an alert classification was properly identified as an adverse event.

20. The method of claim 19, further comprising:
assigning a true positive if the alert classification was properly identified as associated with a higher risk period of data.

21. The method of claim 20, further comprising:
assigning a false positive rating if the alert classification was improperly identified as associated with a high risk period of data.

22. The method of claim 14, wherein classifying portions of data as associated with alerts comprises marking the data with a marker indicating the presence or the absence of an adverse event, and wherein the adverse event is an estimated early cardiac decompensation event.

* * * * *